United States Patent
Xalter et al.

(10) Patent No.: US 9,019,475 B2
(45) Date of Patent: Apr. 28, 2015

(54) METHOD AND DEVICE FOR MONITORING MULTIPLE MIRROR ARRAYS IN AN ILLUMINATION SYSTEM OF A MICROLITHOGRAPHIC PROJECTION EXPOSURE APPARATUS

(71) Applicant: Carl Zeiss SMT GmbH, Oberkochen (DE)

(72) Inventors: Stefan Xalter, Oberkochen (DE); Yim-Bun Patrick Kwan, Aalen (DE); Andras G. Major, Oberkochen (DE); Manfred Maul, Aalen (DE); Johannes Eisenmenger, Ulm (DE); Damian Fiolka, Oberkochen (DE); Jan Horn, Munich (DE); Markus Deguenther, Aalen (DE); Florian Bach, Oberkochen (DE); Michael Patra, Oberkochen (DE); Johannes Wangler, Koenigsbronn (DE); Michael Layh, Altusried (DE)

(73) Assignee: Carl Zeiss SMT GmbH, Oberkochen (DE)

(*) Notice: Subject to any disclaimer, the term of this patent is extended or adjusted under 35 U.S.C. 154(b) by 0 days.

(21) Appl. No.: 14/255,302

(22) Filed: Apr. 17, 2014

(65) Prior Publication Data
US 2014/0233006 A1 Aug. 21, 2014

Related U.S. Application Data

(63) Continuation of application No. 13/556,408, filed on Jul. 24, 2012, which is a continuation of application (Continued)

(30) Foreign Application Priority Data

Feb. 6, 2007 (DE) .......................... 10 2007 005 875
Aug. 2, 2007 (DE) .......................... 10 2007 036 245

(51) Int. Cl.
*G03F 7/20* (2006.01)
*G02B 26/08* (2006.01)
(Continued)

(52) U.S. Cl.
CPC ........ *G03F 7/70058* (2013.01); *G03F 7/70516* (2013.01); *G03F 7/70133* (2013.01);
(Continued)

(58) Field of Classification Search
CPC .................. G01M 11/30; G01N 21/55; G02B 26/0833–26/085; G03F 7/70116; G03F 7/70113; G03F 7/702; G03F 7/70291; G03F 7/70483; G03F 7/70491; G03F 7/70508; G03F 7/70516; G03F 7/7055; G03F 7/7085
USPC ...................... 355/67, 77; 356/139.07, 139.1; 359/298, 855, 904; 700/121
See application file for complete search history.

(56) References Cited

U.S. PATENT DOCUMENTS

| 4,814,829 A | 3/1989 | Kosugi et al. |
| 6,140,653 A | 10/2000 | Che |

(Continued)

FOREIGN PATENT DOCUMENTS

| EP | 1 262 836 | 12/2002 | |
| JP | 2002/353105 | 12/2002 | ............ H01L 21/027 |

(Continued)

OTHER PUBLICATIONS

Japanese Office Action, with English translation, for corresponding JP Appl No. 2009-547617, dated May 29, 2012.

*Primary Examiner* — Colin Kreutzer
(74) *Attorney, Agent, or Firm* — Fish & Richardson P.C.

(57) ABSTRACT

Microlithographic illumination system includes individually drivable elements to variably illuminate a pupil surface of the system. Each element deviates an incident light beam based on a control signal applied to the element. The system also includes an instrument to provide a measurement signal, and a model-based state estimator configured to compute, for each element, an estimated state vector based on the measurement signal. The estimated state vector represents: a deviation of a light beam caused by the element; and a time derivative of the deviation. The illumination system further includes a regulator configured to receive, for each element: a) the estimated state vector; and b) target values for: i) the deviation of the light beam caused by the deviating element; and ii) the time derivative of the deviation.

26 Claims, 8 Drawing Sheets

Related U.S. Application Data

No. 12/506,364, filed on Jul. 21, 2009, now Pat. No. 8,339,577, which is a continuation of application No. PCT/EP2008/000920, filed on Feb. 6, 2008.

(60) Provisional application No. 61/015,999, filed on Dec. 21, 2007, provisional application No. 60/954,150, filed on Aug. 6, 2007.

(51) Int. Cl.
 *G01M 11/00* (2006.01)
 *G01N 21/55* (2014.01)

(52) U.S. Cl.
 CPC ........ *G03F 7/70291* (2013.01); *G02B 26/0833* (2013.01); *G03F 7/70116* (2013.01); *G03F 7/7085* (2013.01); *G01M 11/30* (2013.01); *G03F 7/702* (2013.01); *G01N 21/55* (2013.01); *Y10S 359/904* (2013.01)

(56) References Cited

U.S. PATENT DOCUMENTS

| | | |
|---|---|---|
| 6,421,573 B1 | 7/2002 | Kafka et al. |
| 6,577,429 B1 | 6/2003 | Kurtz et al. |
| 6,737,662 B2 | 5/2004 | Mulder et al. |
| 6,753,528 B1 | 6/2004 | Nikoonahad |
| 6,965,119 B2 | 11/2005 | Sandstrom et al. |
| 8,446,579 B2 | 5/2013 | Tanitsu et al. |
| 8,456,624 B2 | 6/2013 | Tanitsu et al. |
| 2001/0012101 A1 | 8/2001 | Mulkens |
| 2001/0019518 A1 | 9/2001 | Levich et al. |
| 2003/0038225 A1 | 2/2003 | Mulder et al. |
| 2003/0225465 A1* | 12/2003 | Oettinger ................ 700/52 |
| 2004/0053148 A1 | 3/2004 | Morohoshi |
| 2004/0057034 A1 | 3/2004 | Zinn et al. |
| 2004/0100629 A1 | 5/2004 | Stokowski et al. |
| 2004/0114123 A1 | 6/2004 | Mulder et al. |
| 2004/0207386 A1 | 10/2004 | Durr |
| 2005/0068510 A1 | 3/2005 | Bleeker et al. |
| 2005/0134819 A1 | 6/2005 | De Jager |
| 2005/0168790 A1 | 8/2005 | Latypov et al. |
| 2005/0237375 A1* | 10/2005 | Tokita et al. ................ 347/224 |
| 2006/0001855 A1 | 1/2006 | Lof et al. |
| 2006/0050261 A1 | 3/2006 | Brotsack |
| 2006/0103827 A1 | 5/2006 | Derksen |
| 2007/0057164 A1* | 3/2007 | Vaughnn et al. ................ 250/216 |
| 2007/0165202 A1 | 7/2007 | Koehler et al. |
| 2007/0273853 A1 | 11/2007 | Bleeker et al. |
| 2008/0079930 A1 | 4/2008 | Klarenbeek |
| 2008/0192224 A1 | 8/2008 | Gruner et al. |
| 2008/0259304 A1 | 10/2008 | Dierichs |
| 2009/0002668 A1 | 1/2009 | Rohe et al. |
| 2009/0097007 A1 | 4/2009 | Tanaka |
| 2009/0262324 A1 | 10/2009 | Patra et al. |
| 2010/0020300 A1 | 1/2010 | Bouman et al. |
| 2010/0265482 A1 | 10/2010 | Schubert et al. |
| 2010/0283984 A1 | 11/2010 | Layh et al. |
| 2010/0283985 A1 | 11/2010 | Layh et al. |
| 2011/0012010 A1 | 1/2011 | Major |

FOREIGN PATENT DOCUMENTS

| | | | |
|---|---|---|---|
| JP | 2003-508825 | 3/2003 | |
| JP | 2005-136387 | 5/2005 | |
| JP | 2005-223228 | 8/2005 | |
| JP | 2006-024924 | 1/2006 | |
| JP | 2006-133432 | 5/2006 | |
| JP | 2006-148107 | 6/2006 | |
| JP | 2006-269802 | 10/2006 | |
| JP | 2007-212678 | 8/2007 | |
| JP | 2008-091907 | 4/2008 | |
| JP | 2010-034553 | 2/2010 | |
| JP | 2013-175753 | 9/2013 | ............ H01L 21/027 |
| WO | WO 01/18606 | 3/2001 | |
| WO | WO 2005/026843 | 3/2005 | |
| WO | WO 2005/096098 | 10/2005 | |
| WO | WO 2008/061681 | 5/2008 | ................ G03F 7/20 |
| WO | WO 2009/145048 | 12/2009 | ............ G01M 11/00 |

* cited by examiner

METHOD AND DEVICE FOR MONITORING MULTIPLE MIRROR ARRAYS IN AN ILLUMINATION SYSTEM OF A MICROLITHOGRAPHIC PROJECTION EXPOSURE APPARATUS

CROSS-REFERENCE TO RELATED APPLICATIONS

This application is a continuation of, and claims benefit under 35 USC 120 to, U.S. application Ser. No. 13/556,408, filed Jul. 24, 2012, which is a continuation of U.S. application Ser. No. 12/506,364, filed Jul. 21, 2009, which is a continuation of, and claims benefit under 35 USC 120 to, international application PCT/EP2008/000920, filed Feb. 6, 2008, which claims benefit of German Application No. 10 2007 005 875.8, filed Feb. 6, 2007; German Application No. 10 2007 036 245.7, filed Aug. 2, 2007; U.S. Ser. No. 60/954,150, filed Aug. 6, 2007 and 61/015,999, filed Dec. 21, 2007. The contents of international application PCT/EP2008/000920, U.S. application Ser. No. 12/506,364 and U.S. application Ser. No. 13/556,408 are incorporated by reference herein in their entirety.

FIELD

The disclosure relates to illumination systems of microlithographic projection exposure apparatus, in which arrangements of beam deviating elements, such as micromirror arrays, are used for variable illumination of a pupil surface.

BACKGROUND

In illumination systems of microlithographic projection exposure apparatus, which are used for the production of finely structured semiconductor components, flat arrangements of beam deviating elements can be used to manipulate the projection light to try to improve the imaging properties of the microlithographic projection exposure apparatus. One example of this involves so-called multi-mirror arrays, in which a multiplicity of micromirrors are arranged in an array, such as in rows and columns. The micromirrors are movable, such as tiltable about two axes provided perpendicularly to one another, so that their surface normal can be tilted into any directions starting from a neutral position. This can allow for variable alterations in the illumination settings in illumination systems.

SUMMARY

In some embodiments, the disclosure provides a device and a method by which the angle setting of mirror elements of a multi-mirror array can be ascertained effectively. For example, deviations of projection light that strikes a multiplicity of flatly arranged beam deviating elements can be detected and measured, and these deviations can therefore be monitored and regulated. Because variations of the surface of optical elements, such as the shape or alignment of surface regions, for example due to thermal loads or the like, are generally of interest for monitoring the imaging properties and possibly correcting imaging errors, many other applications may be envisaged for such methods and devices.

In some respects, the basic concept of the disclosure is that in addition to the projection light of the illumination system, to which the flat arrangements of beam deviating elements are exposed, at least one measurement light beam from a measurement illumination instrument is directed onto the beam deviating elements to be examined, so that the deviation of the measurement light beam due to the beam deviating element can be recorded by a detector instrument. If it is assumed that the deviation of the measurement light beam by the beam deviating element and the deviation of the projection light incident thereon correlate with one another, then the deviation of the projection light or the change thereof relative to a specified setting can be ascertained by this separate measuring instrument. With the additional provision of a separate measurement illumination instrument which generates the corresponding measurement light beam, the extraction of useful light from the projection light can be obviated, while checking and determination of deviation changes of the optical element to be examined can furthermore be carried out continuously during use of the microlithographic exposure apparatus. This can involve merely the arrival direction of the measurement ray bundle or bundles being different from the arrival direction of the projection light beam or beams, so that no mutual interference takes place.

An angle variation of the surface normal of an optical element's mirror surface to be examined, or the alignment of a corresponding mirror surface, may be monitored and examined by such a procedure.

A method and the device can be used for the examination of mirror elements, such as the aforementioned multi-mirror arrays (MMAs).

The arrival direction of the measurement ray bundle may differ both in the incidence angle with respect to the optical element's surface to be examined, and in an azimuthal incidence direction. The term azimuthal incidence direction is intended here to mean rotation of the incidence plane of the corresponding ray relative to a predetermined plane, for example an incidence plane arranged in a north-south alignment.

If the incidence directions of the measurement light beam and the projection light do not differ in the azimuthal incidence direction, then they at least differ in the incidence angle to avoid mutual interference and make it possible for the measurement light beam reflected from the mirror surface to be recorded by a detector system.

If the incidence direction of the measurement light beam and the incidence direction of the projection light beam or beams do differ in the azimuthal incidence direction, then there may also be a difference in the incidence angle of the optical element to be examined. This is not however compulsory.

A difference of the arrival direction of the measurement light beam from the arrival direction of the projection light beam or beams in the azimuthal incidence direction is often desired, in which case rotation angles in the range of more than 30°, such as more than 60°, and in particular a mutual rotation angle of 90° around the surface normal of the optical element to be examined, are possible. In the case of a 90° arrangement between the incidence plane of the measurement light and the incidence plane of the projection light, a particularly large installation space can be provided for arranging the measurement illumination instrument and a correspondingly arranged detector instrument.

In order to ensure defined illumination of the optical element to be examined with measurement light, and likewise to permit defined recording of the changes in the measurement light due to the interaction with the surface of the optical element, an optical system may respectively be provided between the illumination source and the optical element to be examined on the one hand, and/or between the optical element to be examined and the corresponding detector instrument on the other hand.

The measurement light may have any suitable wavelength, and lie either in the visible or in the invisible range. In general, light will be intended to mean any electromagnetic radiation.

The optical system of the measurement illumination source may include one collimator or a multiplicity of collimators, such as in the form of a perforated plate with an upstream microlens array, so that corresponding collimated measurement light beams are generated.

These collimated measurement light beams are reflected by the surface to be examined and, by converging lenses correspondingly arranged in front of the position sensors of the detector instrument, such as a lens array of converging microlenses, they may be imaged into the focal plane of the corresponding converging lenses as a far-field diffraction image or Fourier transform. Corresponding position sensors may be provided there in the focal plane, for example 4-quadrant detectors or two-dimensional position-sensitive sensors, which establish a deviation of the light cone striking the detector from a neutral position, which corresponds to a determined alignment of the surface of the optical element to be examined.

In order to obtain more installation space, additional optics may be provided between the optical element to be examined and the detector instrument, which make it possible to arrange the detector instrument far away from the optical element to be examined. Optics may furthermore be provided which allow variable arrangement of the detector instrument with simultaneous sharp imaging of a surface region of the optical element to be examined. To this end, the corresponding imaging optics can be configured so that the optical element's surface region to be examined is imaged onto optical lenses assigned to the position sensors while satisfying the Scheimpflug condition.

At the same time, the corresponding optics desirably ensure that the incidence direction of the measurement light beam on the converging detector lenses of the detector instrument corresponds to the alignment of the associated surface regions of the optical element, or the tilt angle of the mirror elements of a multi-mirror array. This may, for example, be ensured by relay optics having two converging lenses.

The angular alignment of the mirror surface of an optical element may be determined continuously during use of the optical element, or the illumination system in which the optical element is arranged. The ascertained values may therefore be used for active control or regulating of manipulable beam deviation elements, for example micromirrors of a multi-mirror array.

BRIEF DESCRIPTION OF THE DRAWINGS

Further advantages and features of the disclosure will become clear from the following detailed description of exemplary embodiments with the aid of the appended drawings, in which.

DETAILED DESCRIPTION

1. Structure of a Projection Exposure Apparatus

Figure 1:
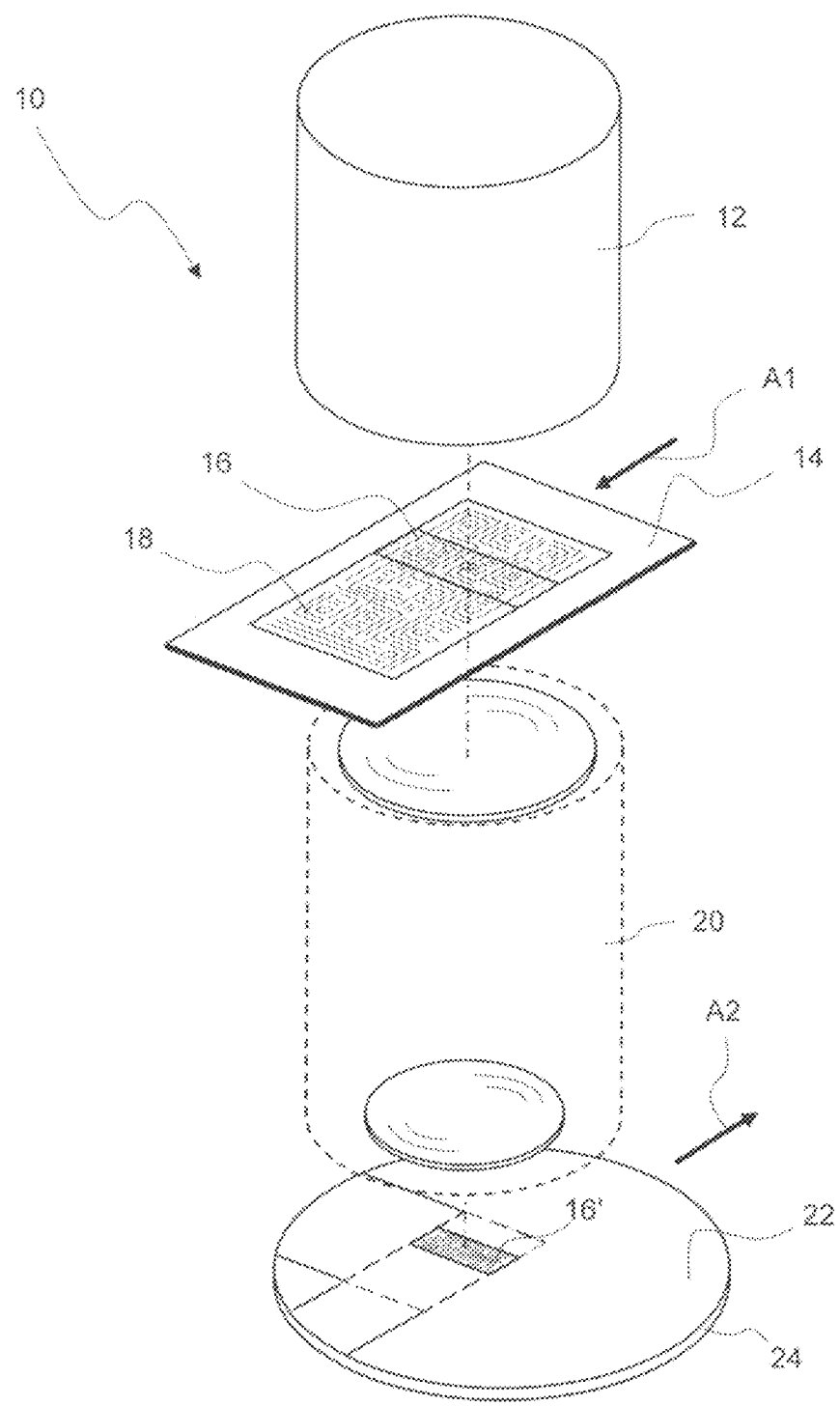
FIG. 1 shows a highly simplified perspective representation of a microlithographic projection exposure apparatus.

FIG. 1 shows a highly schematised perspective representation of a projection exposure apparatus 10, which is suitable for the lithographic production of microstructured components. The projection exposure apparatus 10 contains an illumination system 12 which illuminates a narrow illumination field 16, which is rectangular in the exemplary embodiment represented, on a mask 14 arranged in the so-called mask plane. The illumination system 12 contains a light source, by which projection light can be generated. Conventional light sources are for example excimer lasers with the laser media KrF, ArF or $F_2$, by which projection light with the wavelengths 248 nm, 193 nm and 157 nm can respectively be generated.

Structures 18 on the mask 14, which lie inside the illumination field 16, are imaged with the aid of a projection objective 20 onto a photosensitive layer 22. The photosensitive layer 22, which may for example be a photoresist, is applied on a wafer 24 or another suitable substrate and lies in the image plane of the projection objective 20, which is also referred to as the wafer plane. Since the projection objective 20 generally has an imaging scale $|\beta|<1$, the structures 18 lying inside the illumination field 16 are imaged on a reduced scale as 16'.

The performance of such a projection exposure apparatus is determined not only by the projection objective 20, but also by the illumination system 12 which illuminates the mask 14. Besides the intensity of the light beam striking the mask 14, its illumination angle distribution also has an effect on the quality with which the structures 18 contained in the mask 14 are imaged onto the photosensitive layer 22. Depending on the direction and size of the structures 18 to be imaged, different illumination angle distributions have been found to be advantageous. Since various masks 14 are intended to be imaged by the projection exposure apparatus 10, an illumination system with which different illumination angle distributions can readily be adjusted would be ideal. To this end it is desirable for a pupil surface of the illumination system 12, which crucially determines the illumination angle distribution, to be illuminated as variably as possible by a drivable optical element.

2. Measurement Principle

Figure 2:
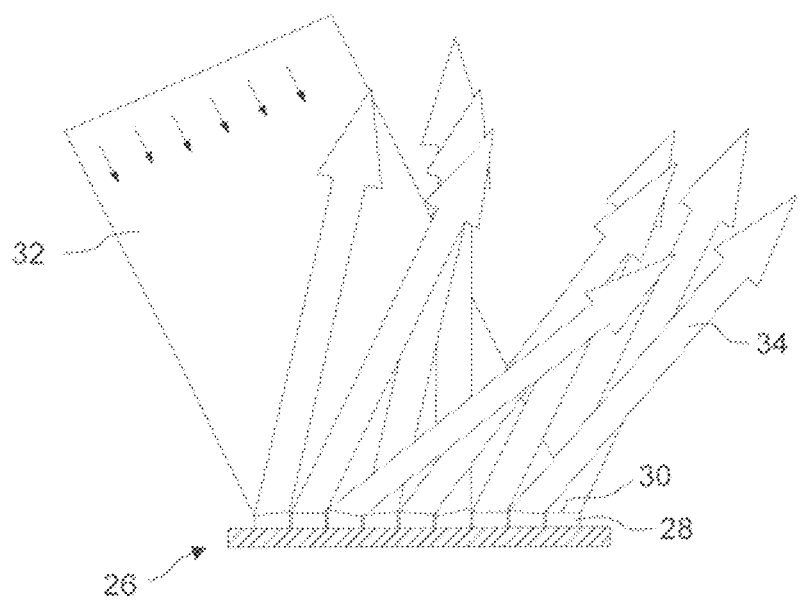
FIG. 2 shows a side view of an optical element to be examined in the form of a multi-mirror array.

FIG. 2 shows a schematic side view of an example of such an optical element, for the monitoring and control of which the device or the method may be used. The optical element in FIG. 1 is a so-called multi-mirror array 26 that includes a multiplicity of small mirror elements 28 which are arranged movably, such as tiltably, so that the mirror surfaces 30 of the mirror elements 28 arranged, for example, next to one another in rows and columns can be aligned differently. Incident projection light 32 can therefore be distributed by reflection from the mirror surfaces 30 into a multiplicity of reflected projection light beams 34, the propagation directions of which can be selected freely by tilting the mirror surfaces 30 within predetermined limits. The term tilting in this context is intended to be understood as a rotation movement about an axis which may essentially extend centrally through a mirror element 28, at its edge or even outside the mirror element 28, so that the alignment of the mirror surface 30 changes with respect to the incident projection light 32. The latter two alternatives are also often referred to as "swivelling". Depending on the embodiment of the mechanical suspensions and actuators of the mirror elements 28, combinations of translation and rotation movements, which will be referred to below likewise for the sake of simplicity as "tilting movements", are also used in order to achieve a change in the alignment of the mirror elements 28 and consequently also the propagation direction of the reflected projection light beam 34.

In many systems, the incident projection light 32 is furthermore subdivided into individual light beams by using microlens arrays before striking the mirror surfaces 30, and is focused onto the mirror elements 28.

Such a multi-mirror array 26 may then be used in an illumination system 12 of a microlithographic projection exposure apparatus 10 for variable illumination of the pupil surface, also abbreviated to pupil illumination. To this end the incident projection light 32 is deviated by a sufficiently large number of mirror elements 28 so that a desired light distribution is generated in the pupil surface. The number of mirrors has an essential effect both on the spatial fluctuations of the light intensity and on the minimum diameter of the reflected projection light beams 34, from the superposition of which the pupil illumination is formed. Optical design calculations have shown that at least 4000 mirrors are desirable in order to obtain an intensity distribution in the pupil plane, which is comparable in respect of its properties with that of a conventional diffractive optical element. Since very small variations in the tilt angles of the mirror elements 28 have large effects on the pupil illumination and therefore on the illumination angle distribution on the mask 14, the disclosure proposes to ascertain the exact angle positions of the mirror surfaces 30 by measuring technology.

Figure 3:
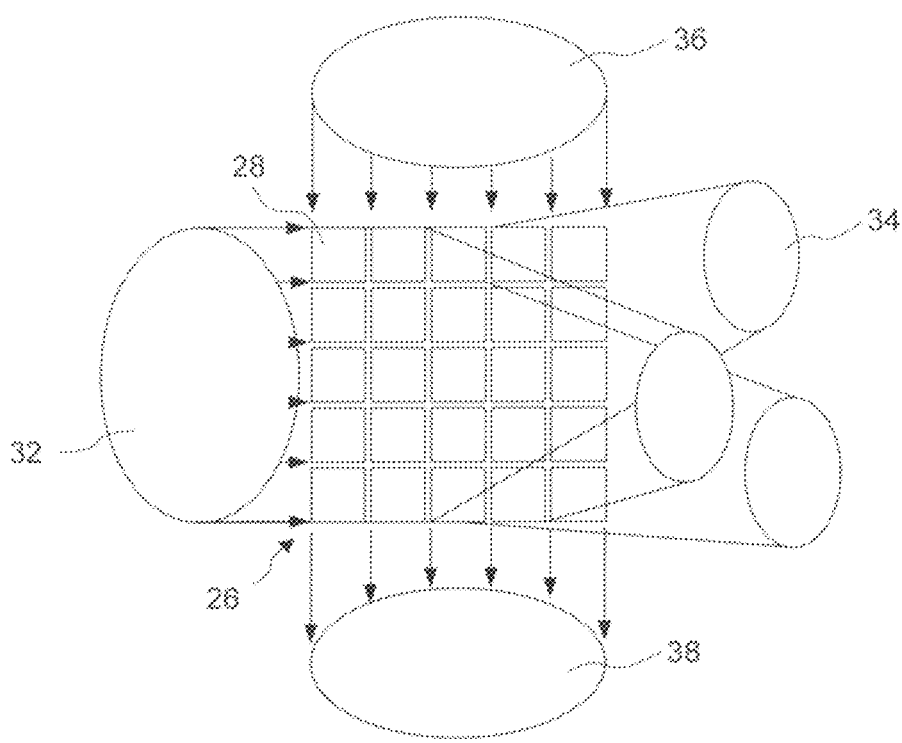
FIG. 3 shows a plan view of the optical element to be examined in FIG. 1, with a representation of the measuring arrangement.

As may be seen in FIG. 3, in addition to the incident projection light 32 i.e. the useful light used to illuminate the mask 14 from the illumination system 12 (also referred to as the objective ray bundle), an additional measurement illumination device is provided which directs measurement light 36, for example in the form of at least one measurement ray bundle, onto the mirror elements 28 of the multi-mirror array 26. Depending on the exemplary embodiment, to this end the measurement illumination may generate one or more measurement light beams or measurement ray bundles which are directed onto the mirror elements 28 either in a scanning fashion, i.e. successively, or simultaneously for some or all of the mirror elements 28. Since the incidence directions of the measurement light beams are known, conclusions can be drawn about the alignment of the reflecting mirror surfaces 30 by measuring the emergence directions of the reflected measurement light beams. This utilises the fact that the deviation of the projection light 32 is correlated with the deviation of the measurement light 36. The reflected measurement light 38 consequently contains information about the tilt status and therefore about the alignment of the mirror elements 28. In the measuring arrangement represented in FIG. 3, the measurement light 36 is directed onto the mirror elements 28 in a plane which is rotated by 90° about the surface normal of the reflecting mirror surfaces 30 relative to the incidence plane of the incident projection light 32.

Continuous measurement of the alignment of the mirror elements 28 is therefore possible even during operation of the illumination system 12. This does not therefore entail down times of the projection exposure apparatus 10 for determining the alignment of the mirror elements 28. Since a fraction of the incident projection light 32 is not used for determining the alignment of the mirror elements 28, no light loss which could reduce the throughput of the projection exposure apparatus 10 is incurred.

Figure 4:
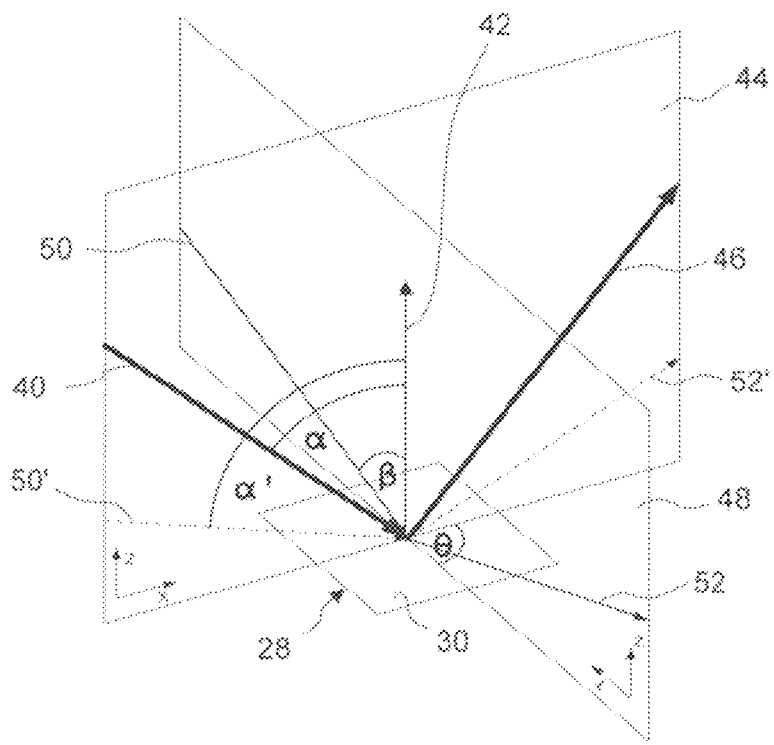
FIG. 4 shows a perspective representation of a measuring arrangement.

FIG. 4 shows a prospective representation of details of the measurement principle. As FIG. 4 reveals, the incident projection light 32 strikes the mirror surface 30 of a mirror element 28 at a particular incidence angle $\alpha$ along an incidence direction 40. Together with the surface normal 42 of the mirror surface 30, the incidence direction 40 of the incident projection light 32 spans the incidence plane (xz plane) 44, in which the emergence direction 46 of the reflected projection light beam 34 also lies according to the reflection law.

According to the representation of FIG. 3, in a yz plane 48 which is rotated azimuthally about the surface normal 42 by a rotation angle $\theta$ of the order of 90° relative to the incidence plane 40 of the projection light 32, incident measurement light 36 is directed along an incidence direction 50 onto the mirror surface 28 and is radiated after reflection by the mirror surface 28 as reflected measurement light 38 along an emergence direction 52 in the direction of a detector instrument. In this solution, the incidence direction 50 of the measurement light 36 therefore differs from the incidence direction 40 of the projection light 32 at least in the azimuthal incidence direction, i.e. in the incidence plane. In addition or as an alternative, the measurement light 36 may also strike the mirror surface 30 at a different incidence angle from the projection light 32.

This is represented by way of example for an incidence direction 50' of the measurement light 36, which lies in the same incidence plane 44 as that in which the projection light 32 strikes the mirror element 28, but makes an incidence angle $\alpha'$ with the surface normal 42 which differs from the incidence angle $\alpha$ of the incidence direction 40 of the projection light 32. The reflected measurement light 38 is therefore also radiated by the mirror element 28 along an emergence direction 52' at a different angle from the projection light 32. This arrangement with the incidence direction 50' of the incident measurement light 36 and the emergence direction 52' of the reflected measurement light 38 also constitutes a solution.

3. Exemplary Embodiments of Measuring Instruments

Figure 5:
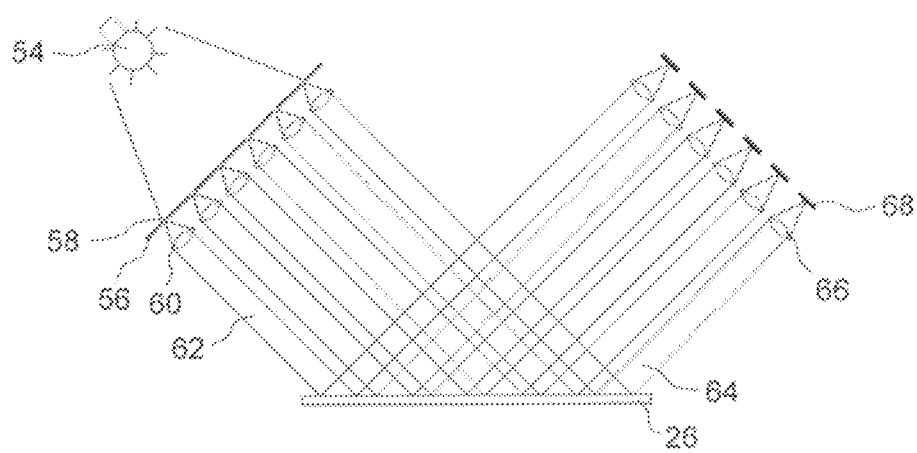
FIG. 5 shows a side view of a measuring instrument.

FIG. 5 shows an exemplary embodiment of a measuring instrument in which a light source 54 of the measurement illumination instrument directs light onto a perforated plate 56. A multiplicity of point light sources 58 are generated by the perforated plate. Downstream converging collimator lenses 60, which are or may be combined in the manner of a microlens array, respectively form a collimator and thereby generate a collimated measurement light beam 62 from the light produced by the associated point light source 58. The measurement light beams 62 generated by the various converging collimator lenses 60 can travel parallel to one another.

As an alternative to this, a single measurement light beam 26 may be scanned over the multi-mirror array 26 by two galvanometer scanners or a combination of one polygon scanner and one galvanometer scanner. The light source, for example a VCSEL (see below), may also be pulsed so that the light source only illuminates when a mirror element 28 is found. The regions between the mirrors do not therefore contribute to the signal which is recorded in a time-resolved way by the detector instrument.

The collimated measurement light beams 62 strike the mirror surfaces 28 to be examined in the multi-mirror array 26, where they are deviated in different directions as a function of the alignment of the mirror surfaces 28. The reflected measurement light beams 64 strike a microlens array which contains a multiplicity of converging detector lenses 66, in whose rear focal plane position sensors 68 of a detector instrument are arranged. Owing to this arrangement the angles, at which the reflected measurement light beams 64 strike the converging detector lenses 66, are in a Fourier relation with the position of the focal points on the position sensors 68, onto which the reflected measurement light beams 64 are focused.

Since these angles of the reflected measurement light beams 64 depend according to the aforementioned reflection law on the alignment of the respectively associated mirror elements 28 of the multi-mirror array 26, by recording the position of the focal points on the position sensors 68 it is therefore possible to determine the alignment of the mirror elements 28. For example, 4-quadrant detectors or two-dimensional position-sensitive sensors may be used as position sensors 68. In this way, for example, a tilt angle range of from ±2 to ±3° for the mirror elements 28 can be ascertained relative to a predetermined surface alignment.

If the mirror surfaces 30 of the mirror elements 28 have a curvature, then measurement light beams 62 may be directed onto different points of the same mirror element 28. This may be done simultaneously or successively, in the manner of a scanning method, even with the same measurement light beam 62. The curvature can then be determined from the different deviations of the measurement light beams 62 for the various points of the mirror surface 30. Another possibility for determining the curvature consists, for example, by determining the focal point diameter of a measurement light beam 62 coming from a curved mirror surface 30 on the position sensor 68, in determining the beam's divergence and therefore the curvature of the mirror surface 30, if it is assumed that the divergence of the incident measurement light 36 is known.

By integration and temporal comparison of a signal on the position sensor 68, with the assumption of a light source with constant intensity, a possible change in the reflection coefficient of the mirror surfaces 30 may furthermore be measured and degradation of the mirror layer may be inferred.

Figure 6:
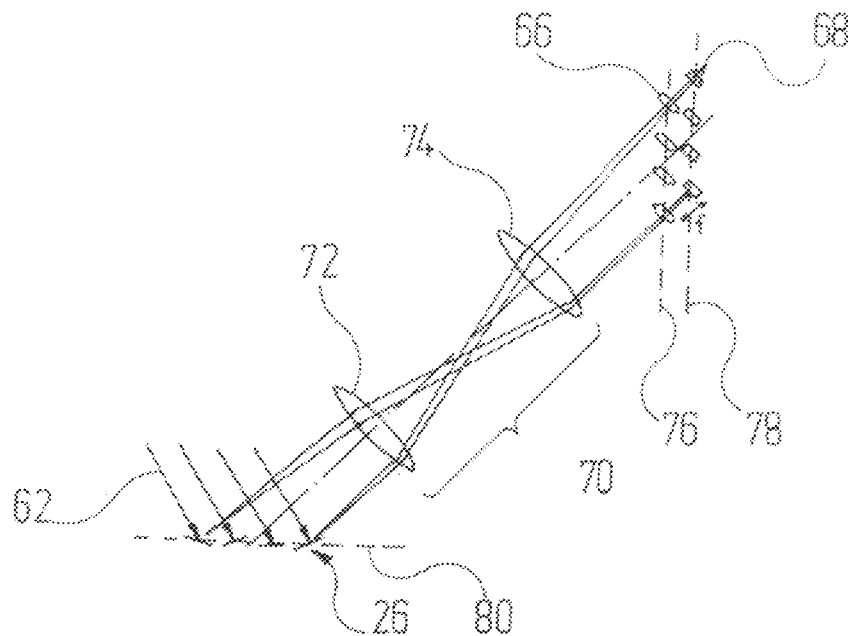
FIG. 6 shows a side view of a measuring instrument.

In order to be able to arrange the detector unit with the position sensors 68 and the upstream microlens array with the converging detector lenses 66 at some distance from the multi-mirror array 26, according to an exemplary embodiment according to FIG. 6, additional relay optics 70 are provided. The relay optics 70, which are represented purely schematically by two converging lenses 72 and 74, image the multi-mirror array 26 onto the arrangement of converging detector lenses 66. The relay optics 70 permit a larger distance from the optical element's surface(s) to be examined, in this case the mirror surfaces 30, without restricting the angle range to be examined. The relay optics 70 therefore decouple the detected angle range of the tilt from the distance of the position sensors 68 from the multi-mirror array 26. In this way, the measuring instrument may be arranged outside the beam path of the illumination system 12, where sufficient installation space is available.

In the exemplary embodiment shown in FIG. 6, the position sensors 68 and the microlens array with the converging detector lenses 66 are arranged in planes 76 and 78 which satisfy the Scheimpflug condition with respect to a plane 80, in which the multi-mirror array 26 is arranged. The Scheimpflug condition is satisfied when the principal plane of the relay optics 70 intersects in one axis with the plane 76 of the converging detector lenses 66 and the plane 80, in which the mirror elements 28 of the multi-mirror array 26 extend. Compliance with this condition, despite the planes 76 and 80 arranged mutually inclined, makes it possible for them to be imaged sharply onto one another. Such an arrangement can therefore image a large region of the surface of the optical element to be examined, or a multiplicity of the mirror elements 28, equally sharply onto the converging detector lenses 66 of the microlens array, and it allows a corresponding angular arrangement of the detector instrument. With such an arrangement the plane 80 in which the mirror elements 28 extend, which is inclined to the optical axis, can be imaged sharply onto the converging detector lenses 66 of the microlens array.

Similarly as in the exemplary embodiment of FIG. 5, the position of the focal point formed on the position sensor 68 changes as a function of the incidence angle, at which the associated measurement light beam 64 strikes the converging detector lens 66. Owing to the imaging by the relay optics 70, however, this incidence angle is in turn proportional to the tilt angle of the associated mirror surface, the alignment of which is intended to be measured. Here again, through deviations of the focal point in the position sensor 68 from a neutral position, which corresponds to a predetermined alignment of the mirror surface 30, it is therefore possible to draw conclusions about the tilt angle of the relevant mirror surface 30.

The disclosure makes it possible to determine the alignment of the mirror elements 28 of the multi-mirror array 26 during operation of the projection exposure apparatus. In the event of deviations of the measured alignment from a setpoint direction, the relevant mirror element 28 may be readjusted until the desired setpoint alignment is achieved. This is a prerequisite for active control or regulating of the mirror elements 28, as will be explained in more detail below.

4. Encapsulation of the Multi-Mirror Array

Figure 7:
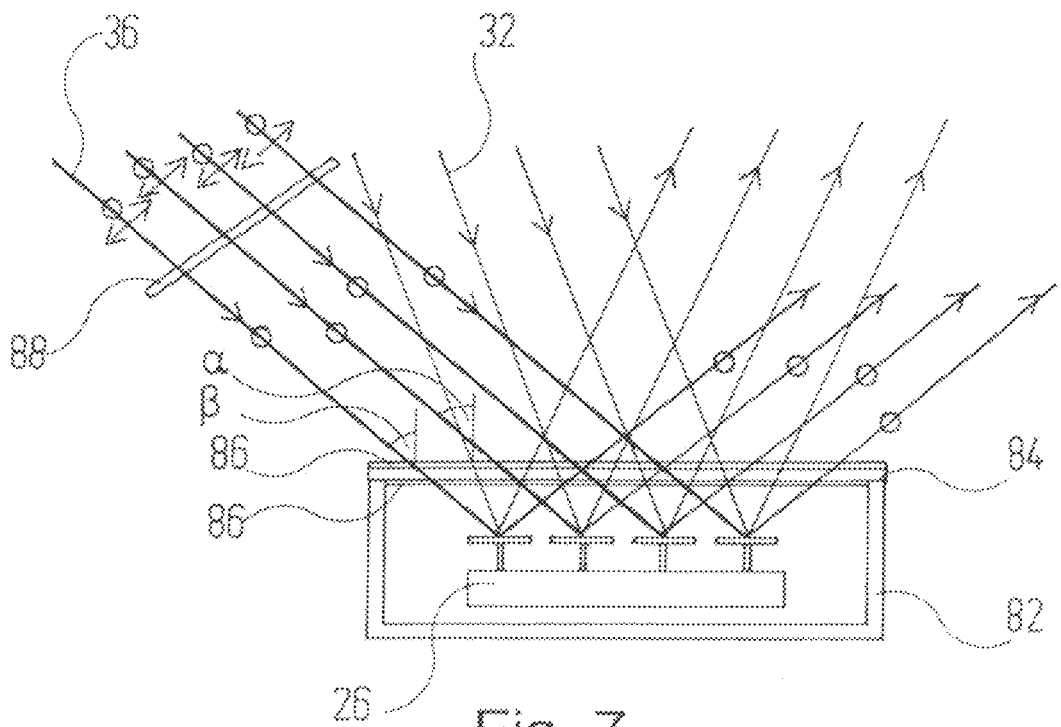
FIG. 7 shows a side view of a multi-mirror array encapsulated in a housing.

FIG. 7 shows a highly simplified representation of a multi-mirror array 26 which, in order to protect against external effects, for example pressure or temperature variations, is encapsulated in a housing 82 inside the illumination system 12. The housing 82 has a transparent window 84, through which the incident projection light 32 and the measurement light 36 can strike the individual mirror elements 28 of the multi-mirror array 26. After the individual ray bundles have been deviated according to the alignment of the mirror elements 28, they pass through the transparent window 84 of the housing 82 in the opposite direction.

In order to reduce undesirable reflections and concomitant intensity losses, the transparent window 84 bears one or more antireflection coatings 86 which are conventionally adapted to the wavelength of the light passing through and the angles occurring. In the exemplary embodiment, the antireflection coating 86 is designed so that the incident projection light 32, which arrives at the angle α, can pass through the transparent window 84 with the least possible intensity loss.

So that the incident measurement light 36 which usually has a different wavelength, and under certain circumstances as explained above strikes the multi-mirror array 26 at a different angle β, can also pass through the transparent window 84 without causing perturbing reflections, a polariser 88 is inserted into the beam path of the incident measurement light 36. The polarisation direction of the incident measurement light 36 is in this case selected so that the measurement light 36 is essentially p-polarised in relation to the incidence plane of the measurement light 36 on the transparent window 84.

The measurement illumination instrument is furthermore arranged so that the incidence angle β of the incident measurement light 36 is at least approximately equal to the Brewster angle. This is because if light strikes the interface of two optical media at the Brewster angle, then the reflected light will contain only the s-polarised component of the incident light. The p-polarised component of the incident light is then refracted fully into the other optical medium. Since the incident measurement light 36 is entirely p-polarised in the present case, and it does not therefore contain an s-polarised component which could be reflected, the intensity of the reflected light beam with incidence at the Brewster angle is zero and no measurement light 36 will therefore be reflected at the transparent window 84. With approximate incidence at the Brewster angle, i.e. in the range of 5° around the Brewster angle, the reflected intensity is somewhat less than 5% of the incident intensity owing to partial reflection of the p-polarised component. The incident measurement light 36 can therefore pass through the transparent window 84 virtually without losses, even though the antireflection coatings 86 are optimised only for the incident projection light 32 but not for the incident measurement light 36. It is however advantageous for the wavelength of the incident measurement light 36 to be greater than the thickness of the antireflection coatings 86, which have been optimised for the incident projection light 32, since in this case the antireflection coatings 86 have no effect on the incident measurement light 36.

Although the angles of the emerging ray bundles no longer correspond to the Brewster angle after reflection by the mirror elements 28 of the multi-mirror array 26, they are however close to the Brewster angle owing to the small tilt angles of ±2-3° of the mirror elements 28, so that a reduction of the undesirable reflections is also to be observed in the emerging ray bundles.

The encapsulated multi-mirror array 26 described in connection with FIG. 7 may furthermore be configured with gas tight encapsulation, so that the mirror elements 28 of the multi-mirror array 26 are enclosed by an inert gas which is contained in the housing 82. As an alternative, the housing 82 may be provided with gas connections (not shown in FIG. 7) in order to exchange the inert gas. The gas exchange may take place continuously, i.e. event during illumination of the multi-mirror array 26 with measurement light 36 and/or projection light 32. As an alternative, the gas exchange of the inert gases may also take place when the multi-mirror array 26 is not being illuminated with measurement light 36 and/or projection light 32.

All gases or gas mixtures which prevent a reaction on the mirror surfaces 30 of the mirror elements 28 of the multi-mirror array 26, or which delay it so that the mirror elements 28 are not compromised or at least not essentially compromised in their reflection properties during their intended service life, i.e. their reflection behaviour (for example their reflection coefficient) does not change by more than 10% during this period, are suitable as an inert gas. For the possible reactions of the mirror surfaces 30 or the coatings used there, the light wavelength and the light intensity with which the multi-mirror array 26 is operated should in particular also be taken into account. The inert gas used may also depend on the light wavelength and the light intensity.

Since the mirror surfaces 30 usually have coatings to increase the reflection, and degradation of such a coating may take place in air depending on the coating material or the coating materials, for example by reaction with the oxygen in air, degradation is prevented by encapsulation of the multi-mirror array 26 by the housing 82 and a suitable inert gas contained therein. Furthermore, many more materials may be employed for the coating of the mirror surfaces 30 since any reaction of the coating materials with air is prevented owing to the encapsulation of the mirror elements 28 and the use of inert gases. For example aluminium, amorphous or crystalline silicon, chromium, iridium, molybdenum, palladium, ruthenium, tantalum, tungsten, rhodium, rhenium, germanium may be used as coating materials or as a material for the mirror elements 28, and coatings of mixtures of these materials may furthermore be produced. For example helium, argon or other noble gases, nitrogen or mixtures of these gases may be used as inert gases. Furthermore, the gases employed may also be used for temperature control of the multi-mirror array 26, for example in order to cool it during exposure to measurement light 36 and/or projection light 32. The transparent window 84 of the housing 82 which encloses the multi-mirror array 26 may include amorphous or crystalline quartz or for example calcium fluoride, or consist of these materials, depending on the wavelength used and depending on the intensity used for the measurement light 36 and/or the projection light 32.

As an alternative to the use of an inert gas as described above in the housing 82 which encloses the multi-mirror array 26, this may also be evacuated or the gas or gas mixture may be modified in respect of its pressure or its composition. By evacuating the housing 82 or by modifying the gas pressure or the gas composition, an interfering reaction on the mirror surfaces 30 of the mirror elements 28 of the multi-mirror array 26 may likewise be prevented or delayed so that the mirror elements 28 are not significantly compromised in their reflection properties during their intended service life.

5. Determination of the Alignment by Pattern Recognition

Figure 8:
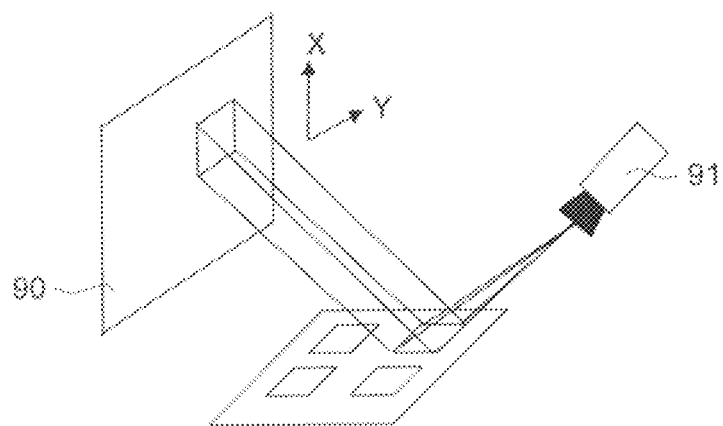
FIG. 8 shows a perspective representation of an exemplary embodiment in which the tilts of the individual mirror elements of a multi-mirror array are recorded with the aid of a camera.

FIG. 8 shows another possibility for determining the alignment of the mirror elements of the multi-mirror array 26. In this case a pattern, for example a luminous pattern, is reflected by the multi-mirror array 26 and imaged in a camera 91. The luminous pattern may for example be generated by illuminating a semi-reflective screen 90 which carries the pattern, or by illumination through a transparent sheet (similarly to a photographic slide).

Figure 9:
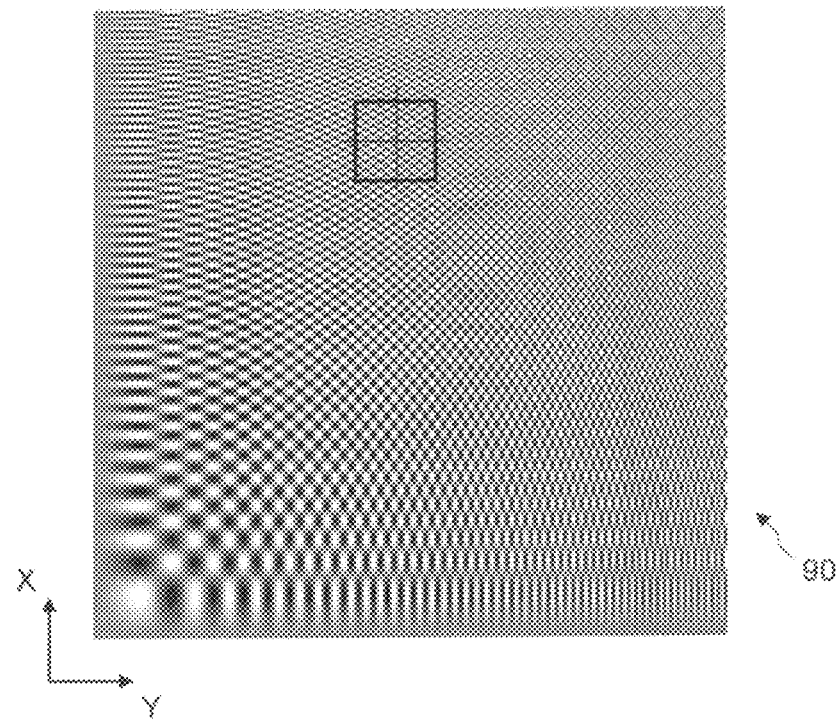
FIG. 9 shows a representation of a pattern which is suitable for use in the exemplary embodiment represented in FIG. 8.

FIG. 9 shows a pattern suitable for the purposes of the disclosure by way of example. The pattern has a chequerboard alternation between bright and dark, the frequency of which increases continuously along the two screen axes x_screen and y_screen so that no two regions of the screen 90 have an identical pattern. If a detail of the camera image which corresponds to a mirror element 28 is observed, then a different region of the pattern will be visible in this detail depending on the tilt of the mirror element 28. With the aid of an evaluation unit which, for example, carries out an autocorrelation between the detail of the camera image and the known pattern of the screen 90, the exact tilt of the mirror element 28 can thus be recorded. Since the camera can be arranged so that it records a plurality of mirror elements 28 and each mirror element 28 individually shows a region of the screen pattern, the tilts of a plurality of mirror elements 28 can be determined simultaneously by this instrument.

Instead of an ordered pattern as shown in FIG. 9, a random pattern may also be selected so long as it has an autocorrelation function which is as narrow as possible.

Another possibility consists in providing different colour profiles along the two screen axes x_screen and y_screen, and thus achieving colour coding of the different positions of the screen. In theory, a colour-sensitive camera 91 or another colour-sensitive sensor with only one pixel would then be sufficient in order to determine the tilt angle of the mirror elements 28 by the method explained above. Since the colour vector or RGB vector is already provided directly in commercially available digital colour cameras, the evaluation would also be extremely simple and not very computation-intensive.

6. Calibration

First Exemplary Embodiment

Figure 10:
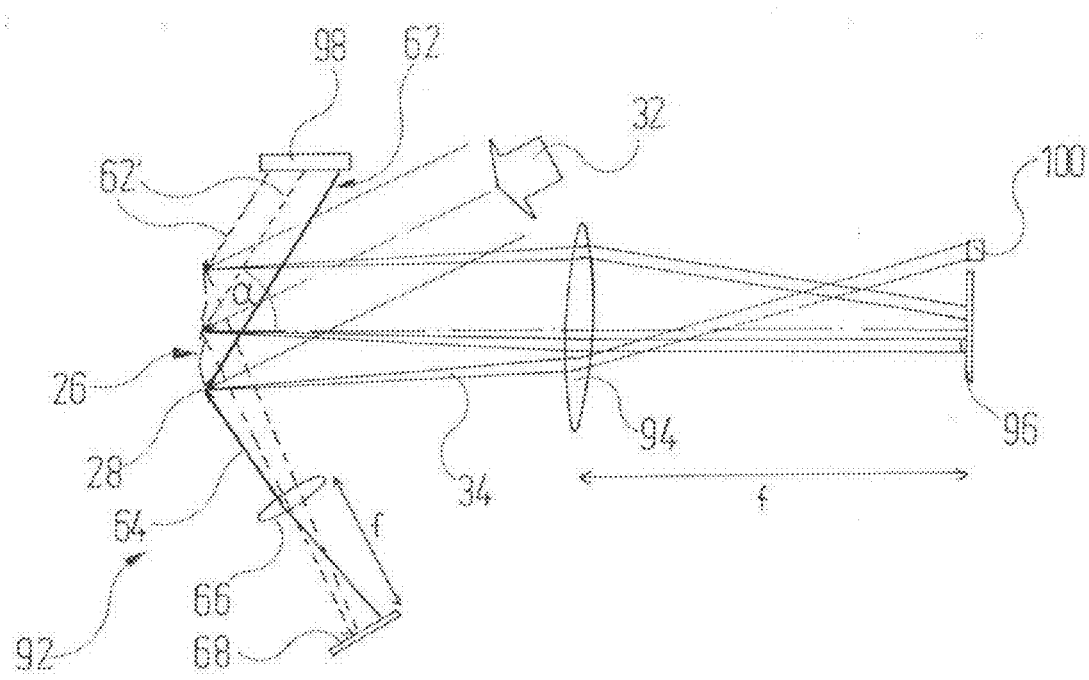
FIG. 10 shows a side view of an illumination system with a multi-mirror array.

FIG. 10 shows a simplified representation of an arrangement which allows calibration of the measuring instrument according to a first exemplary embodiment. The calibration constitutes a comparison between the actual beam deviations of the reflected projection light 34, which is intended to illuminate the pupil plane of the illumination system 12 with the desired intensity distribution, and the signals recorded by the measuring instrument. The calibration presented here may, however, also be used when the signals which describe the alignment of the mirror elements 28 are provided not by the measuring instrument described above, but by other sensors or measuring instruments. In this context, for example, electromechanical, piezoresistive, inductive, capacitive or optical sensors arranged for example on the multi-mirror array 26, which so to speak record the tilt angle from the "inside", may be envisaged.

In a pupil shaping part 92 represented in a very simplified way in FIG. 10, of an illumination system 12, the projection light 32 generated by a projection light source, for example an excimer laser, strikes a multi-mirror array 26 and is directed after reflection thereon through pupil optics 94 into the pupil plane 96 of the illumination system 12. Since the packing density of a multi-mirror array 26 suitable for such a purpose does not conventionally exceed 90%-95%, so that there are no segments or no undesirably reflecting segments between the individual mirror elements 28, in this exemplary embodiment the incident projection light 32 is focused by microlens arrays in smaller projection light beams onto the mirror elements 28, as is known per se in the prior art, for example from WO 2005/026843 A2.

Via a separate beam path, a collimated measurement light beam 62 is furthermore directed at a larger angle α' onto the multi-mirror array 26. In the present exemplary embodiment, the measurement illumination instrument includes an arrangement of a plurality of semiconductor lasers, which emit light from their flat semiconductor surface. With such a so-called VCSEL array 98 (vertical cavity surface emitting laser array), each individual mirror element 28 of the multi-mirror array 26 can be deliberately illuminated with a collimated measurement light beam 62. To illustrate the individual switchability, the beam path of two temporarily extinguished measurement light beams 62' is represented by dashes in FIG. 10. After reflection by the multi-mirror array 26, the measurement light beams 62 strike a position sensor 68, which is arranged in the focal plane of the converging detector lens 66, as reflected measurement light beams 64 via a converging detector lens 66. Owing to the converging detector lens 66, an angle change of the reflected measurement light beams 64 causes a displacement of the focal points on the position sensor 68 onto which the reflected measurement light beams 64 are focused.

In order to calibrate the measuring instrument, the arrangement furthermore has a projection light detector 100 which is arranged at a precise predetermined position in the pupil plane, but in immediate proximity near the usable pupil aperture, such as at a distance of less than one fifth of the diameter of the pupil aperture. If the measurement of the tilt angles of an individual mirror element 28 is now to be calibrated, then only the corresponding mirror element 28 is tilted until the projection light beam 34 reflected by it strikes the projection light detector 100 in the pupil plane. If a measurement light beam 26 is simultaneously directed onto the mirror element 28 to be calibrated, then the focal point's position thereby established on the position sensor 68 can be stored as a calibration value in an evaluation unit.

In order to record nonlinearities, such as may be caused for example by the pupil optics 94 or by curved mirror surfaces 30, it is advantageous to arrange a plurality of projection light detectors 100, such as four of them, around the pupil aperture. The projection light detectors 100 may also be designed as 4-quadrant detectors.

Once the tilt angles of each mirror element 28 have been calibrated in the way described above, the measuring instrument may be used to monitor the tilt of the mirror elements 28 and therefore the illumination of the pupil plane during operation of the illumination system 12, in order to readjust the mirror elements 28 if need appropriate. In general, such readjustment will be expedient since high-frequency perturbations in the range of from 100 Hz to 1000 Hz, such as may be caused for example by vibrations of the mirror elements 28 due to air currents or acoustic waves, would lead to intolerable errors in the illumination of the pupil plane.

Incorrect illuminations, which result from slow drift movements between the mirror elements 28 of the multi-mirror array 26 and the microlens array which focuses the projection light 32 onto the mirror elements 28, may furthermore be recorded by the described calibration method. These will initially not be recorded by the measuring instrument, since it is subject to other drift movements. Since an individual mirror element 28 may be aligned at the projection light detector 100 even during operation of the illumination system 12, without thereby substantially affecting the illumination of the pupil plane, the calibration may be repeated gradually at particular time intervals for each mirror element 28 during operation. The slow drift movements will thereby be recorded and corrected. Depending on how large the fraction of the projection light extracted from the normal beam path of the illumination system 12 can be, the time intervals may be varied or individual mirror elements 28, some mirror elements 28 or all of the mirror elements 28 may be calibrated simultaneously in this way.

7. Calibration

Second Exemplary Embodiment

Figure 11:
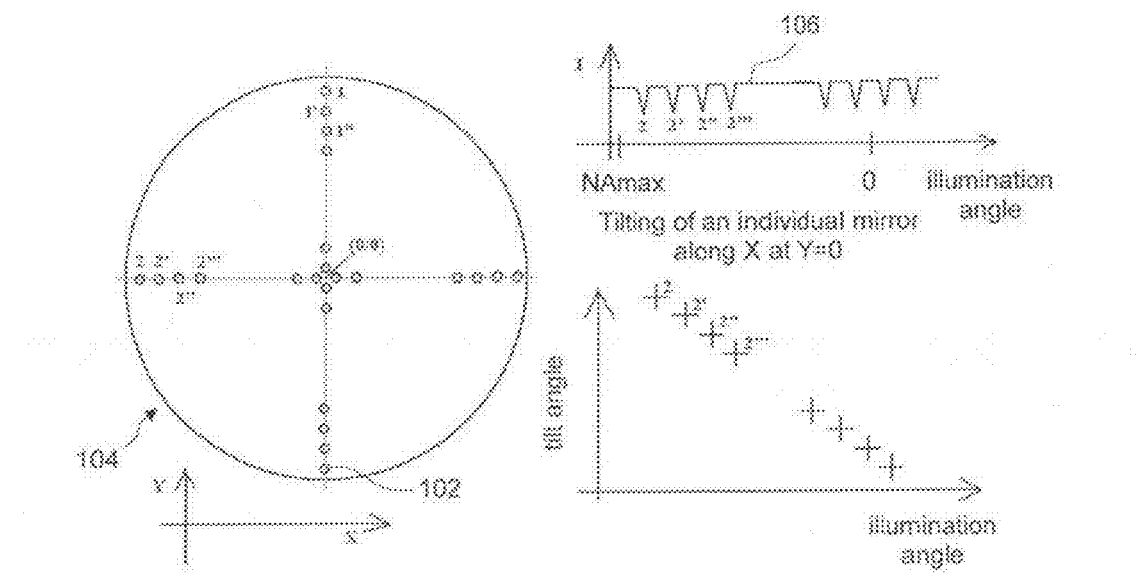
FIG. 11 shows a summary of a calibrating instrument, which represents on the one hand a calibration plate and on the other hand and the intensity profile during the movement of a mirror element and the relation determined therefrom between the mirror element angle and the system angle.

FIG. 11 illustrates an overview representation of another method for calibrating the measuring instrument described in detail above. The calibration method according to this exemplary embodiment may also be used independently of the measuring instrument. Use may therefore be envisaged when the signals, which contain information about the alignment of the mirror elements 28, are provided not by the measuring instrument described above but by other sensors or measuring instruments.

For example, the calibration method of this exemplary embodiment may advantageously be used in order to directly calibrate the control variables for driving the mirror elements 28, if a so-called feed-forward operation of the multi-mirror array 26 is selected, in which separate sensor or measuring instruments are not necessarily provided for feedback. As will become clear from the explanations below, this is based on the fact that the proposed calibration method may be repeated rapidly with little outlay in order to recalibrate possible slow-acting processes such as drift, electrical charges, etc., and may even be carried out for individual mirror elements during an exposure process of the exposure apparatus 10.

According to this exemplary embodiment, regions 102 with a reduced transmission of 50% are generated at particular positions of the pupil surface. To this end, for example, a transparent arc calibration plate 104 may be arranged in or in the vicinity of the pupil surface. The reduced-transmission regions 102 respectively have the size of a light spot generated in the pupil surface by a reflected projection light beam 34. They form a kind of calibration scale, which is arranged either fixed in relation to the optical axis of the illumination system 12 or replaceably at an accurately established position and angularly precisely aligned. By suitable methods, the reduced-transmission regions 104 may also be arranged on or in elements which are already present, for instance in the pupil optics 94.

In order to calibrate a mirror element 28, an intensity sensor is fitted into a field plane, for example the objective plane or the image plane of the projection objective 20. The intensity sensor records the intensity profile 106 while an individual mirror element 28 illuminates different positions of the pupil surface by the reflected projection light beam 34 assigned to it along predetermined paths, for example along a coordinate axis (see the graph at the top right in FIG. 11). Such an intensity profile 106 is represented by way of example in FIG. 11 for a movement of a mirror element 28, in which the light spot migrates centrally over the pupil surface along the X axis, i.e. beyond the optical axis. If the reflected projection light beam 34 coming from the mirror element 28 strikes a reduced-transmission region 104, then this will be registered as a drop in intensity by the intensity sensor.

With the aid of suitable arrangements of the reduced-transmission regions 102 and a corresponding evaluation unit, which records the minima of the intensity profile 106 and assigns them to particular positions inside the pupil surface with knowledge of the arrangement of the regions 104, the measurement signals of the measuring instrument which simultaneously measures the alignment of the mirror elements can thereby be calibrated. A relationship will thereby be found between the tilt angle of the mirror elements 28, as determined by the measuring instrument, and the absolute angle position of the illumination angle of the projection light 32, as indicated in the graph at the bottom right in FIG. 10.

In an advantageous refinement, an angle-resolving intensity sensor will be used instead of a normal intensity sensor in a field plane. In this way it is possible to establish not only whether light is actually striking a point in the field plane, but also the directions from which light is striking this point. Since different directions in the field plane are associated with the positions in the pupil surface, a plurality of mirror elements 28 may even be calibrated simultaneously by such an angle-resolving intensity sensor. The respectively illuminated reduced-transmission regions 102 should then lie as far apart from one another such that the intensity sensor can still resolve the associated directions in the field plane with sufficient accuracy.

In order to prevent local intensity drops from occurring in the reduced-transmission regions 102 on the pupil surface during projection operation of the projection exposure apparatus 10, twice as many reflected projection light rays 34 as would otherwise be provided will respectively be directed onto regions 102 to be illuminated. Since the transmission of these regions 102 is 50% as indicated above, the doubled number of projection light rays 34 therefore generates the desired intensity. In this way, a homogeneous intensity distribution can be generated in the pupil surface despite the statically used calibration plate 104.

A transmission reduction by 50% takes place in the exemplary embodiment described above, such reduced-transmission regions 102 then having been illuminated with twice the number of mirrors, i.e. with twice the number of reflected projection light beams 34, in projection operation. The reduced-transmission regions 102 may also be reduced to 1/n, where n is an integer greater than or equal to 2. In this case, the respective reduced-transmission region 102 will then be illuminated with n reflected projection light beams 34 in projection operation.

These embodiments are recommendable when the individual reflected projection light beams 34 have approximately the same intensity. If the intensities of the individual reflected projection light beams 34 differ substantially from one another, however, then n may also be a number other than an integer. In this case the reduced-transmission regions 102 will be illuminated with a plurality of reflected projection light beams 34 in projection operation, so that the desired intensity in the field plane is achieved for the angles assigned to the reduced-transmission regions 102.

As an alternative to this, the calibration plate 104 may be removed from the beam path during normal projection operation.

8. Regulation

First Exemplary Embodiment

So far, devices and methods have been described which are suitable for determining the tilt angle of the individual mirror elements 28 of a multi-mirror array 26. Once information about the tilt angles has become available, then it is desirable to ensure by a regulating system that a particular setpoint value for the tilt angle is complied with as accurately as possible. The average value of all the neutral settings of the beam deviating elements can be adjusted with an accuracy of 1/6000. Relative settings with respect to this neutral setting should furthermore be adjustable with an accuracy of at least 1/500.

The adjustment time $L_{set}$, in which the mirror elements 28 are desirably aligned, is established by the times within which the pupil illumination is intended to be modified for viable operation of the microlithographic projection exposure apparatus 10. These times typically lie in the range of 10 ms-50 ms. This has a direct effect on the bandwidth of the regulating system, i.e. the frequency with which the tilt angles of the mirror elements 28 are intended to be measured and adjusted.

For a multi-mirror array 26 in which it is possible to rule out individual mirror elements 28 being excited in vibration by neighbouring mirror elements 28 or external effects, under certain circumstances active attenuation may be obviated if the mechanical properties of the multi-mirror array 26 are stable enough for so-called forward-feed control.

Repeated calibration of the individual mirror elements 28 will nevertheless often be expedient, since the relationship between the normal vectors nv of the mirror surfaces 30 and the applied control signals sv may change over time owing to various effects. This relationship can be expressed by the equation nv=K(t)*sv. The quantity K(t) in the most general case is a tensor, since the control signals sv may also affect one another, for example by electrostatic charges. If the time dependency of the tensor K itself depends on external parameters p, for instance the temperature, then these effects may be measured by a separate measurement pickup (for example a thermometer). The tensor is then a function not only of time t, but also of the parameters p (i.e. K=K(t,p)). The tensor K(t,p) may then be employed for determining the control signals sv, without another calibration having to be performed.

Yet since in general nondeterministic effects can never fully be suppressed, repeated calibration may nevertheless be desirable. With an adjustment time of 10 ms, a calibrating rate of 1 kHz (i.e. one tenth of the adjustment time) may be desirable for a calibration measurement of a tilt angle of an individual mirror element 28 for viable feed-forward control.

For a multi-mirror array 26 in which vibrations due to internal or external interference can no longer be ruled out, a closed control loop is recommendable instead. Typical natural frequencies of 1-2 kHz for the tilt oscillations of the mirror elements 28 imply measurement and regulating rates of 1-2 kHz (e.g., 10-20 kHz) for each relevant coordinate of an individual mirror element 28. In a multi-mirror array 26 with at least 4000 mirror elements 28, this leads to a measurement rate of more than 4 MHz per coordinate, such as tilt angles or translations.

To this end it is possible to use a control loop which, depending on the measuring device sensor signal received, acts directly on the control variables s for controlling the tilt angle of the mirror element 28 so that the setpoint value of the tilt angle is complied with as accurately as possible. For such a purpose, a so-called PID regulator is conventionally used which receives the regulating difference e as an input signal, i.e. the deviation between the setpoint value and the actual value of the mirror angle. Depending on the setting of the proportional (P), integral (I) and differential components (D) of the PID regulator, the control variable s is then set accordingly, which in turn affects the actual value of the mirror angle. Such a closed control loop is operated with the so-called regulating frequency f.

In relation to the regulating of the mirror elements 28 of a multi-mirror array 26, however, the following problems arise. On the one hand, differentiation of the sensor signal is often difficult since the sensor values of the measuring instrument are strongly affected by inaccuracy. Differentiation by discrete filters in the regulating element, which is responsible for the differential component (D), may therefore lead to such strong noise amplification that the resultant regulating signal is unusable. On the other hand, the regulating difference e can be calculated only with the sampling frequency at which the measurement values for the tilt angle of the mirror elements 28 are provided. Owing to the large number of mirror elements 28, for example a few thousand or even several tens of thousands of mirror elements 28, the maximum sampling frequency for an individual mirror element 28 is greatly limited. Moreover, the control loop can be likewise operated only with a regulating frequency f which corresponds to this low sampling frequency, which may lead to sizeable deviations from the setpoint value.

Figure 12:
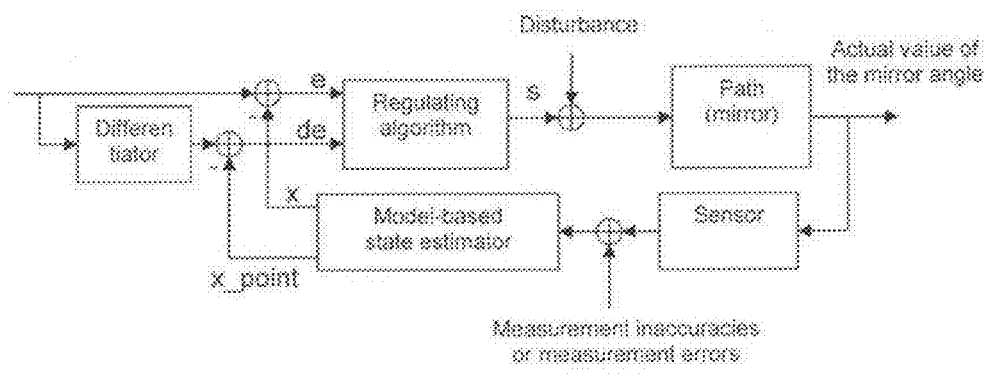
FIG. 12 shows a diagram of a control loop which may be used in order to monitor and control beam deviation elements.

FIG. 12 shows the regulating scheme of a control loop which uses a model-based state estimator, and which does not therefore present the disadvantages mentioned above. The model-based state estimator estimates the current tilt angle of the mirror elements 28 on the basis of a model and with the aid of the sensor signals affected by possible inaccuracies (for example due to the measurement methods). To this end the model-based state estimator calculates the estimated state vector, i.e. for example the estimated tilt angle x and the time derivative x_point of the tilt angle, by an internal model from the sensor signals (affected by inaccuracy). The state vector may also include a plurality of tilt angles and/or other position parameters of a mirror element 28 as well as their dynamic behaviour, for example their time derivative.

This estimated state vector is then compared with the setpoint status of the system, i.e. the actual setpoint value of the tilt angle and its time derivative. Even though the time derivative of the tilt angle is here again determined by differentiation from the setpoint value of the mirror angle, this differentiation presents no problem since the setpoint value of the tilt angle is not affected by inaccuracy. As well as the regulating difference e, the time derivative de of the regulating difference is also obtained from this comparison, and these together form the regulating difference vector (e, de).

Figure 13:
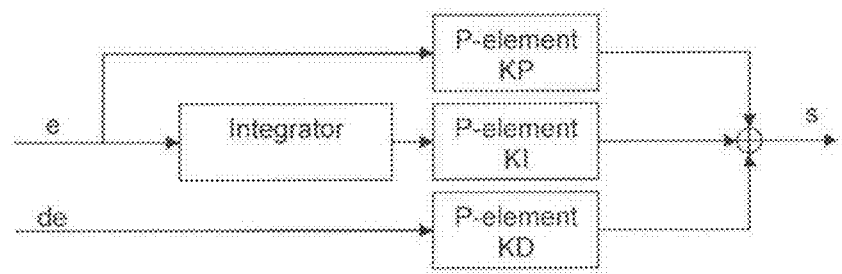
FIG. 13 shows a detailed diagram of the regulating algorithm shown in FIG. 12.

This regulating difference vector (e, de) is now sent to a regulating algorithm which calculates the control variable s and sends it to the controller of the mirror element 28. The regulating scheme of this regulating algorithm is shown in detail in FIG. 13. As may be seen from FIG. 13, the regulating algorithm has three proportional elements by which the effect of the various regulating components can be determined. A first proportional element KP corresponds to the proportional component (P) of a PID regulator, in which the regulating difference e is only multiplied by a constant. A second proportional element KI multiplies the output signal of an integrator, which integrates the regulating difference e, by a constant, and it therefore corresponds to the integral component (I) of a PID regulator. A third proportional element KD corresponds to the differential component (D) of a PID regulator, in which the time derivative de of the regulating difference e, which is sent to the regulating algorithm as explained above, is multiplied by a constant. All three regulator components are added and output as a control variable s.

Owing to the model-based state estimator, such a control loop may even be used in digital form with measurement signals strongly affected by inaccuracy, as is the case with a conventional PID regulator.

As a starting point for producing the model-based state estimator, it is recommendable to use state estimators known from the literature which can be particularly suitable for taking stochastic inaccuracies of the measurement signals into account for the estimation, and to adapt these state estimators according to the desired properties of the specific application. Examples of this are the Kalman filter, the extended Kalman filter (EKF), the unscented Kalman filter (UKF) or the particle filter.

Since such model-based state estimators can even output the estimated state vector (x, x_point) with a rate which is higher than the sampling frequency of the measurement signal, the regulating can be carried out with a high regulating frequency f despite the large number of mirror elements 28 and the concomitant low sampling frequencies of each individual mirror element 28. Sufficient accuracy of the tilt angles of the mirror elements 28 can thereby be achieved.

In the case of a Kalman filter, distinction is made between a kinematic model variant which is based on a Taylor expansion of the current tilt angle, and a dynamic model variant which more precisely replicates the behaviour of the system specifically in the time periods in which no measurement values are provided.

All the regulating elements may furthermore be provided in multiples or in common for regulating a plurality of mirror elements 28. All the regulating variables, for example the control variable s, as a vector whose number of components is equal to the number of mirror elements 28.

Implementation of the control loop by software or on an FPGA chip is also suitable for such an application, since in particular the model-based state estimator can thereby be configured flexibly.

9. Regulation

Second Exemplary Embodiment

One important aspect of an illumination system 12, which has a multi-mirror array 26 for illuminating a pupil surface, is the speed and the accuracy with which the individual mirror elements 28 can be adjusted. The key data for the measuring instrument, which records the tilt of the mirror elements 28, are in this case dictated by the optical and desired mechanical properties for the design of the pupil shaping part 92 of the illumination system 12 and of the illumination system 12 overall.

In some embodiments, the multi-mirror array 26 has in total 64×64=4096 mirror elements 28, which respectively have to be driven separately in two axes and the tilt angles of which need to be measured individually. With the solutions known to date in the prior art, such a large number of mirror elements 28 cannot be adjusted with the requisite accuracy and within the short times dictated by the desired properties for modern projection exposure apparatus 10. This is because each mirror element 28 should be able to adopt a tilt angle of at least ±2°, if possible ±3°, in both axes about a given neutral position, the control system needing to be able to govern this angle range with a systematic accuracy of approximately 11 microradians and a statistical inaccuracy of approximately 140 microradians.

It is therefore desirable to measure the mirror positions and apply corrections by a control loop. A time of approximately 1 ms is in this case available for measuring the entire set of 4096 mirror elements 28, i.e. it is desirably possible to determine the tilt angle of each individual mirror element 28 in approximately 250 ns with the requisite accuracy. The tilt angles of the mirror elements should furthermore be measured respectively with the aid of a measurement light beam 62 (see the exemplary embodiment of FIG. 10), the propagation direction of the reflected measurement light beam 64 after reflection by the mirror surface 30 providing information about the tilt angle. The object is therefore to determine the tilt angle of the reflected measurement light beams 64 rapidly enough.

To this end, as explained above, angles are converted into positions by using Fourier optics, for example the converging detector lens 66, and these positions are recorded on a position sensor 68. Owing to installation space restrictions, however it is possible only with difficulty to use 4096 parallel detector instruments, as shown for the exemplary embodiment of FIG. 5. Thus without sizeable outlay, as is the case in the exemplary embodiment shown in FIG. 10, only one copy of the position sensor 68 and the Fourier optics may respectively be used. With considerable outlay it is possible to install approximately 4 detector instruments, but 4096 detector instruments can hardly be installed at present. The aim is therefore to satisfy the desired properties for the measuring and control instruments with only one position sensor 68 and Fourier optics.

Figure 14:
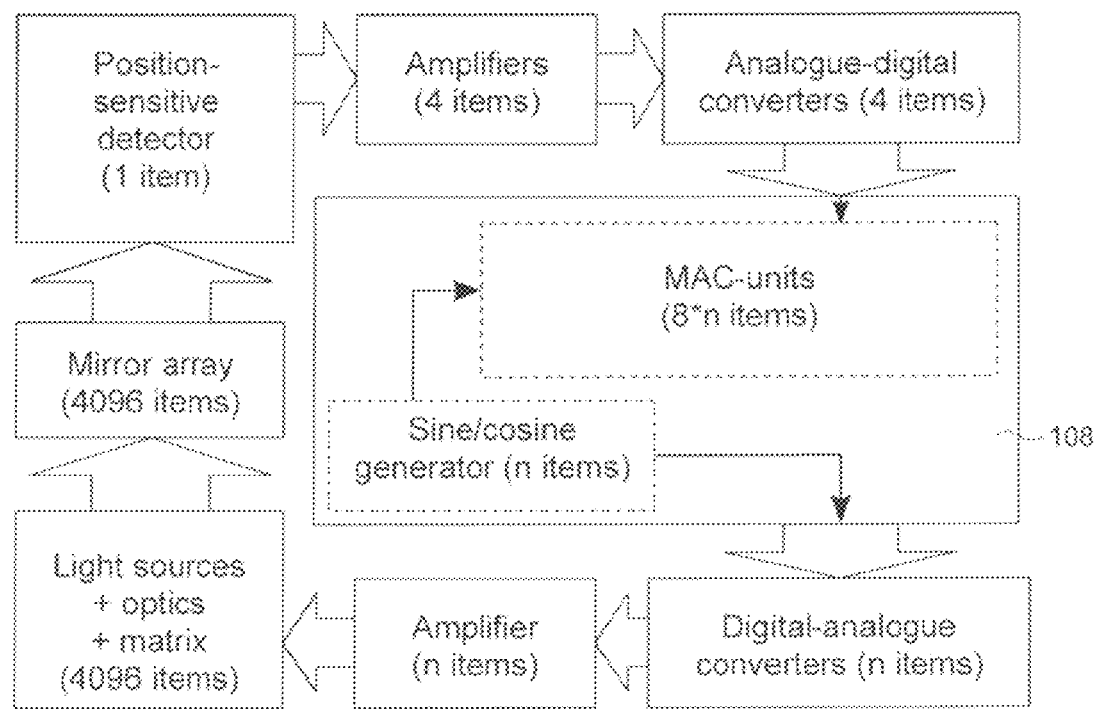
FIG. 14 shows a structural diagram of a measuring instrument which employs a frequency multiplex method.

To this end, FIG. 14 shows the schematic structure of a device that allows a multiplex method, which allows parallel and independent measurement of a plurality of mirror elements 28 with only one position sensor 68.

As mentioned in the exemplary embodiment of FIG. 10, arrangements of laser diodes, so-called VCSEL arrays 98, may be used as light sources for the measurement illumination. Such VCSEL arrays 98 with a square or hexagonal grid of 64×64 grid points are already commercially available. By a matrix drive in which the anodes and cathodes are respectively connected to one another in rows or columns, simultaneous independent control of up to 64 laser diodes is possible, for example within a row. The light from the laser diodes is then focused onto the multi-mirror array 26 by the converging collimator lenses 60 of a microlens array, which is mounted fixed on the VCSEL array 98.

Various commercial solutions may be envisaged for the position sensor 68. Position sensors 68, which are also known as PSDs for short, are already commercially available with a bandwidth of approximately 4 MHz and noise which just still allows the requisite measurement accuracy (for example the 2L4 type from SiTek). Yet since the measurement time per mirror element 28 can only be about 250 ns, this position sensor 68 is already at the limit of its performance with respect to the speed of the measurement. Attempts are therefore already being made to find alternatives for the position sensor 68, which achieve the requisite spatial resolution and allow even shorter measurement times. This disclosure therefore relates to all detector types; the data of the 2L4 PSDs from SiTek may be used as a starting point.

From the published data of PSDs, amplifier circuits and analogue-digital converters, the theoretically achievable statistical position error may be deduced. Since this is somewhat smaller than often desired, it is thus theoretically possible to analyse the mirror elements 28 by time division multiplexing. The laser diodes of the VCSEL array 98 are switched on one after the other, so that only the measurement light beam 64 reflected by one mirror element 28 respectively strikes the position sensor 68. Owing to the finite bandwidths of the laser diodes and the position sensor 68, however, the length of time usable for the measurement is reduced to less than 100 ns. This method will be referred to below as "sequential", because the light sources are switched on strictly one after the other and only one respectively illuminates at a time.

In order to counteract the restricting factors, for example the signal rise time of the position sensor 68, the DC offset and the drift, as well as the 1/f noise of the amplifiers, the laser diodes are not switched on and off one after the other, rather they are operated simultaneously in groups of for example four or eight laser diodes. The intensities of the individual laser diodes of a group, however, are modulated sinusoidally with different frequencies. Owing to the phase-sensitive detection of the electrode currents of the position sensor 68, i.e. its output signals, the components of the various reflected measurement light beams 64 at the different positions of the position sensor 68 are separated according to their modulated frequencies. Simply speaking, the method is similar to a measurement with a plurality of lock-in amplifiers operated in parallel.

This reduces the effect of the signal rise time of the position sensor 68 as a rigid limit for the performance of the measuring instrument. What is more, measurements of the tilt angles of a plurality of mirror elements 28 are therefore possible in the range of the bandwidth and with reduced amplitude. The effect of all DC effects, i.e. offsets, drifts and 1/f noise, is furthermore filtered out. AC coupling of the amplifiers, for example, makes it possible to obviate the differential amplifiers needed for the PSD bias of the position sensor 68, so that their noise is eliminated. The effect of the "dead time", in which the system stabilises and no measurements are possible, is also reduced considerably.

As a side effect of the AC coupling, the quality of the digitisation of the sensor signals of the position sensor 68 is also improved since the most recent generation of analogue-digital converters, which are desired irrespective of the measurement method being used, achieve their highest resolution only with AC coupling.

As a departure from the lock-in principle known per se, the system is modulated not with one frequency but with a plurality of frequencies simultaneously. In this feature, the system is somewhat similar to a Fourier interferometer.

A particular choice of the frequencies and the data acquisition times makes it possible to use strictly periodic boundary conditions. Error-free Fourier analysis even of very short data streams is therefore possible, and it is not necessary to use smoothing or a multiplicative "window" as in the case of lock-in amplifiers.

Although the readily apparent advantages of the described method are also confronted with a few disadvantages, these can easily be overcome:

The maximum light intensity, which a position sensor 68 can process, is limited. The luminance of each individual light source should therefore be reduced when a plurality of light sources are shining at the same time, so that the ratio of signal amplitude to noise is reduced. This amplitude loss is however compensated for by the longer available measurement time, so that the limitation of the maximum light intensity on its own does not entail any additional measurement error.

Based on the choice of frequencies (see below), a bandwidth of more than 4 MHz is desired. The more light sources are modulated simultaneously, the greater is the desired bandwidth. Owing to the finite bandwidth of the position sensor 68, the signal amplitude at high frequencies becomes lower and the statistical error therefore becomes greater.

Correct choice of the measurement frequencies is crucial for successful implementation of the technique. In order to avoid the window problem in the Fourier analysis, the frequencies are selected so that a whole number of periods of each frequency is respectively measured in the measurement interval. The limits of the measurement interval are therefore periodic boundary conditions for all frequencies. A window is not therefore necessary and the measurement signals are exactly orthogonal, which prevents channel crosstalk in the Fourier analysis.

The VCSEL array 98 and its electronics do not exhibit a linear relationship between drive signal and luminosity. In addition to the measurement frequencies, the light field therefore also contains their harmonics. If such harmonics of one laser diode coincide with the measurement frequency of another laser diode (i.e. of another mirror element 28), then the measurement result assigned to this other laser diode will be vitiated. No measurement frequency should therefore be a multiple of another frequency measurement. In order to ensure this, the frequencies are distributed as prime numbers within the bandwidth.

In the specific example, it is essential to achieve a measurement clock of 250 ns per mirror. In the case of four simultaneously active light sources, four frequencies are needed in order to analyse four mirror elements 28 simultaneously. Such a measurement therefore lasts 1 µs (with neglect of the transient time which may be of the order of 200 ns). The periodic boundary conditions are thus applied for frequencies which are multiples of 1 MHz. The first four prime number multiples of 1 MHz are thus frequencies 2 MHz, 3 MHz, 5 MHz and 7 MHz. In the case of eight simultaneous measurements, the interval is 2 µs long and the measurement frequencies are 1, 1.5, 2.5, 3.5, 5.5, 6.5, 8.5 and 9.5 MHz. The optimal choice of the number of frequencies depends on the bandwidth of the position sensor 68. Simulations have shown that the optimum for the Silek 2L4 and the requisite key data lies between four and eight frequencies; the exact value may also be determined experimentally. Since the density of the prime numbers decreases with an increasing value, the bandwidth also increases with an increasing number of measurement frequencies so that the evaluable signal amplitude of the position sensor 68 decreases, which in turn compromises the accuracy.

Owing to the limited total intensity, which can be detected at most on the position sensor 68, the luminosity of the light sources are also desirably selected so that the saturation limit of the position sensor 68 is not exceeded. To this end it is expedient to drive the light sources so that the maximum total intensity is as low as possible, in order that the average power of each individual light source can be set as high as possible. Since the frequencies are established by the prime number distribution and each light source has the same amplitude, the maximum total luminosity can be minimised by adjusting the relative phases. A nonlinear numerical minimisation has shown that a significant reduction in the maximum intensity can be achieved merely by suitable choice of the phases. Expressed in multiples of the individual maximum intensity, the maximum is for example 2.93 for 4 light sources, 4.33 for 6 sources and 5.87 for 8 sources.

A significant advantage of the proposed method, compared with the sequential sampling of the mirror elements (without modulation) as described in the introduction, is that the speed of the position sensor 68 does not represent a fundamental limit for the measurement accuracy. Arbitrarily fast measurements are possible in principle, although measurement accuracy suffers from the decreasing signal amplitude.

However, it is therefore conceivable (and readily achievable by corresponding configuration of the evaluation software in the computation unit) to switch over between different speeds and accuracies upon command. For example, a sampling time of 0.2 ms for all mirrors may be set for the active attenuation of the mirrors, with a correspondingly large measurement error, and it is possible to switch back again into 1 ms with full accuracy for the actual adjustment process. With purely sequential measurement, a measurement frequency of 0.2 ms would no longer be achievable with the SiTek 2L4. Under given conditions (i.e. when sampling times of 0.2 ms are intended to be achieved with the 2L4 from SiTek in order to attenuate actively), this method is therefore not only an advantageous solution, but possibly even the only solution.

The following components are desirable for implementing the measurement method:
 A measurement illumination instrument with a multiplicity of light sources, which is provided with a suitable number of a driver amplifiers so that groups of 4, 6, 8, etc. light sources can be operated simultaneously.
 Signal generators which can generate frequency- and phase-correlated sine signals, their number being equal to the number of light sources driven simultaneously. Generators according to the DDS (direct digital synthesis) principle are highly suitable for this.
 Four analogue-digital converters, which digitise the preamplified signals of the position sensor 68. Since this technique is based on synchronous detection, the clock source of these converters is to be derived from the same reference as the clock of the signal generators.

A computation unit, which can evaluate the sensor signals of the analogue-digital converters. Owing to the nature of the task, it is expedient to use a programmable logic unit in its place, for example an FPGA (field-programmable gate array). The computation unit (FPGA) accordingly has the following main tasks:

Collecting the measurement data of the four A/D converters.

Numerical generation of sine and cosine signals with frequencies equal to those of the light sources.

Multiplication of the sine and cosine signals by the A/D converter data. This gives eight products per frequency used.

Summing the products over the measurement interval. These sums give non-normalized 0° and 90° components, from which the amplitude of the respective input signal can be determined by quadratic addition.

The 2D angle position of the respective mirror is determined from the amplitudes by simple addition, subtraction and division. A comparatively long time is available for these operations, since they only need to be carried out twice per mirror.

By utilising the computation units which are available in modern FPGAs, this task can be performed with moderate outlay in a single FPGA.

The block diagram of the electronic instrument, including the main functions of the FPGA, can be seen in FIG. 14.

Only the computation-intensive operations are indicated in the computation unit 108. "MAC" units are multiplier-adder units, which are provided in an 8*n-fold configuration, n being the number of light sources which are modulated simultaneously with different frequencies. Except for the computation unit 108, which is implemented as "firmware" of an FPGA and is not manifested directly in hardware, the arrangement is very similar to that of a conventional "sequential" measurement method and can therefore be constructed economically. In this diagram, the function of the DDS units has already been integrated substantially into the FPGA (D/A converter, bottom right), although this may also be implemented with conventional DDS components.

10. Concluding Remarks

The measures and devices mentioned above in connection with the illumination of a pupil plane may also readily be used advantageously for active masks, in which arrangements of micromirrors are likewise provided as switchable elements.

The multi-mirror arrays may likewise be replaced by other reflective or transmissive elements, which make it possible to deviate incident light in different directions into different subregions of the element by applying a control signal. Such alternative structures could for example include electro-optical or acousto-optical elements, in which the refractive index can be varied by exposing a suitable material to electrical fields or ultrasound waves. This variation of the refractive index may then be used in order to achieve the desired deviation of the light.

Although the disclosure has been described with the aid of certain exemplary embodiments, it is readily apparent to a person skilled in the art that alternatives or modifications are also possible in relation to the some of the described features and/or different combinations of the proposed features, without departing from the protective scope of the appended claims.

What is claimed is:

1. A monitoring device for monitoring an arrangement of beam deviating elements positioned in a first plane, the device comprising:
   an array of detector elements positioned to receive light from the arrangement of beam deviating elements;
   an optical system positioned between the arrangement of beam deviating elements and the array of detector elements and configured to image the arrangement of beam deviating elements positioned in the first plane to a second plane; and
   an array of detector lenses positioned in the second plane,
   wherein the optical system defines an optical axis that is inclined relative to the first and second planes, and the array of detector elements is positioned in a third plane spaced from and parallel to the second plane.

2. The monitoring device of claim 1, wherein each detector lens in the array of detector lenses is aligned with a corresponding detector element in the array of detector elements.

3. The monitoring device of claim 1, wherein each beam deviating element is a tiltable mirror having a reflecting mirror surface.

4. The monitoring device of claim 1, further comprising an evaluation device coupled to the array of detector elements and configured to provide information about the arrangement of the beam deviating elements based on signals from the array of detector elements.

5. The monitoring device of claim 4, wherein the information about the arrangement of the beam deviating elements comprises information about an alignment of one or more of the beam deviating elements.

6. The monitoring device of claim 4, wherein each beam deviating element comprises a reflecting mirror surface, and wherein the information about the arrangement of the beam deviating elements comprises information about a change in a reflection coefficient of the reflecting mirror surface of one or more of the beam deviating elements.

7. The monitoring device of claim 1, wherein an inclination of the second plane relative to the optical axis is set to sharply image the first plane to the second plane by compensating for an inclination of the first plane relative to the optical axis.

8. An illumination system having a pupil surface, the illumination system comprising:
   a projection light source;
   the monitoring device of claim 1; and
   the arrangement of beam deviating elements,
   wherein:
   the arrangement of beam deviating elements is configured to variably illuminate the pupil surface of the illumination system with projection light from the projection light source,
   each beam deviating element is configured to cause a deviation of a projection light beam incident thereon in response to a control signal applied to the beam deviating element, and
   the illumination system is configured to be used in a microlithographic projection exposure apparatus.

9. The illumination system according to claim 8, wherein the arrangement of beam deviating elements is encapsulated in a housing, the housing having a transparent window through which projection light passes.

10. The illumination system according to claim 9, wherein light incident on the arrangement of beam deviating elements is configured to strike the transparent window at Brewster angle.

11. The illumination system according to claim 10, wherein the monitoring device further comprises a monitoring light source different from the projection light source, and wherein light from the monitoring light source comprises p-polarized light, and a reflected intensity of the p-polarized light at the transparent window is less than 5%.

12. The illuminating system according to claim 9, further comprising antireflection coatings disposed on the transparent window, the antireflection coatings being optimized for the projection light.

13. The illumination system according to claim 8, further comprising a control unit configured to apply the control signal to each beam deviating element to individually drive each beam deviating element.

14. The illumination system of claim 8, wherein the monitoring device further comprises a monitoring light source different from the projection light source, and wherein the monitoring light source is configured to generate the light received by the array of detector elements from the arrangement of beam deviating elements.

15. An apparatus, comprising:
the illumination system according to claim 8; and
a projection objective, wherein the apparatus is a microlithographic projection exposure apparatus.

16. An illumination system having a pupil surface, the illumination system comprising:
a projection light source;
an arrangement of beam deviating elements positioned in a first plane;
a monitoring device for monitoring the arrangement of beam deviating elements, the monitoring device comprising:
an array of detector elements positioned to receive light from the arrangement of beam deviating elements;
an optical system positioned between the arrangement of beam deviating elements and the array of detector elements and configured to image the arrangement of beam deviating elements positioned in the first plane to a second plane; and
an array of detector lenses positioned in the second plane, wherein:
the array of detector elements is positioned in a third plane spaced from and parallel to the second plane;
the arrangement of beam deviating elements is configured to variably illuminate the pupil surface of the illumination system with projection light from the projection light source, and
the illumination system is configured to be used in a microlithographic projection exposure apparatus.

17. An apparatus, comprising:
an illumination system having a pupil surface, the illumination system comprising:
a projection light source;
an arrangement of beam deviating elements positioned in a first plane;
a monitoring device for monitoring the arrangement of beam deviating elements, the monitoring device comprising:
an array of detector elements positioned to receive light from the arrangement of beam deviating elements;
an optical system positioned between the arrangement of beam deviating elements and the array of detector elements and configured to image the arrangement of beam deviating elements positioned in the first plane to a second plane; and
an array of detector lenses positioned in the second plane; and
a projection objective,
wherein:
the array of detector elements is positioned in a third plane spaced from and parallel to the second plane;
the arrangement of beam deviating elements is configured to variably illuminate the pupil surface of the illumination system with projection light from the projection light source, and
the apparatus is a microlithographic projection exposure apparatus.

18. A method for monitoring an arrangement of beam deviating elements positioned in a first plane of an illumination system, the method comprising:
using an array of detector elements to detect light received from the arrangement of beam deviating element; and
determining information about the arrangement of the beam deviating elements based on signals from the array of detector elements,
wherein an optical system is positioned between the arrangement of beam deviating elements and the array of detector elements and images the arrangement of beam deviating elements positioned in the first plane to a second plane, and an array of detector lenses is positioned in the second plane,
wherein the optical system defines an optical axis that is inclined relative to the first and second planes, and the array of detector elements is positioned in a third plane spaced from and parallel to the second plane.

19. The method of claim 18, wherein the information about the arrangement of the beam deviating elements comprises information about an alignment of one or more of the beam deviating elements.

20. The method of claim 19, further comprising regulating the alignment of the beam deviating elements using a control loop, wherein the control loop comprises a model-based state estimator.

21. The method of claim 20, wherein the model-based state estimator estimates a current alignment of the arrangement of the beam deviating elements based on a model and the signals from the array of detector elements.

22. The method of claim 20, wherein the model-based state estimator comprises a Kalman filter that accounts for stochastic inaccuracies of the signals from the array of detector elements.

23. The method of claim 18, wherein each beam deviating element comprises a reflecting mirror surface, and wherein the information about the arrangement of the beam deviating elements comprises information about a change in a reflection coefficient of the reflecting mirror surface of one or more of the beam deviating elements.

24. A method for illuminating a pupil plane in an illumination system of a microlithographic projection exposure apparatus, the method comprising:
using an arrangement of beam deviating elements to variably illuminate the pupil plane of the illumination system of the microlithographic projection exposure apparatus; and
monitoring the arrangement of beam deviating elements using the method of claim 18.

25. The method of claim 24, wherein each beam deviating element is configured to cause a deviation of a projection light beam incident thereon based on a control signal applied to the beam deviating element.

26. The method of claim 24, wherein the beam deviating elements comprise tiltable mirrors having reflecting mirror surfaces.

* * * * *

UNITED STATES PATENT AND TRADEMARK OFFICE
CERTIFICATE OF CORRECTION

| | | |
|---|---|---|
| PATENT NO. | : 9,019,475 B2 | Page 1 of 1 |
| APPLICATION NO. | : 14/255302 | |
| DATED | : April 28, 2015 | |
| INVENTOR(S) | : Stefan Xalter et al. | |

It is certified that error appears in the above-identified patent and that said Letters Patent is hereby corrected as shown below:

In the claims

Column 23

Line 5, in Claim 12, delete "illuminating" and insert -- illumination --

Signed and Sealed this
Twentieth Day of October, 2015

Michelle K. Lee
*Director of the United States Patent and Trademark Office*